United States Patent [19]

Reichl

[11] 4,430,444
[45] Feb. 7, 1984

[54] METHOD OF MAKING METHANOL USING A SLAGGING GASIFIER

[75] Inventor: Eric H. Reichl, Greenwich, Conn.

[73] Assignee: Conoco Inc., Wilmington, Del.

[21] Appl. No.: 356,017

[22] Filed: Mar. 8, 1982

[51] Int. Cl.$^3$ .................. C07C 27/06; C07C 31/04
[52] U.S. Cl. ............................. 518/703; 422/189; 422/235; 518/704; 518/705; 568/910; 568/913
[58] Field of Search .............. 422/189, 235, 148; 518/703, 704, 705; 568/910, 913

[56] References Cited

U.S. PATENT DOCUMENTS

| | | | |
|---|---|---|---|
| 3,950,369 | 4/1976 | Gent | 518/705 |
| 4,087,449 | 5/1978 | Marschner et al. | 518/705 X |
| 4,191,700 | 3/1980 | Lebowitz et al. | 518/705 X |
| 4,195,978 | 4/1980 | Anderson | 48/202 X |
| 4,199,327 | 4/1980 | Hempill et al. | 48/202 |
| 4,218,389 | 8/1980 | Jackson et al. | 518/705 X |
| 4,219,492 | 8/1980 | Konok et al. | 518/705 X |
| 4,348,487 | 9/1982 | Goldstein et al. | 518/705 X |

OTHER PUBLICATIONS

Bowden et al., Synthetic Fuels From Coal, Alternative Energy Sources Symposium, Feb. 9–13, 1980.

*Primary Examiner*—Barry S. Richman
*Attorney, Agent, or Firm*—Dale Lovercheck; William A. Mikesell, Jr.

[57] ABSTRACT

A process for producing methanol from solid carbonaceous material comprising providing a gasifier means and a methanol formation means connected to said gasifier means, said gasifier means comprising a gasification chamber defined by a gasification chamber wall having an upper and a lower portion, an upper chamber wall inlet means for feeding said solid carbonaceous material into said gasification chamber, a lower chamber wall gas injection means for introducing gas into said gasification chamber, and an upper chamber wall gas outlet means, said gas outlet being connected to a gas product conduit, said methanol formation means comprising a methanol formation reactor means, reactor output conduit means, condensor means, and condensor output conduit means, said reactor conduit means being connected to said lower chamber wall gas injection means, said condenser output conduit means being connected to said condenser means and to said methanol formation reactor means, said gas product conduit being connected to said condenser means.

2 Claims, 1 Drawing Figure

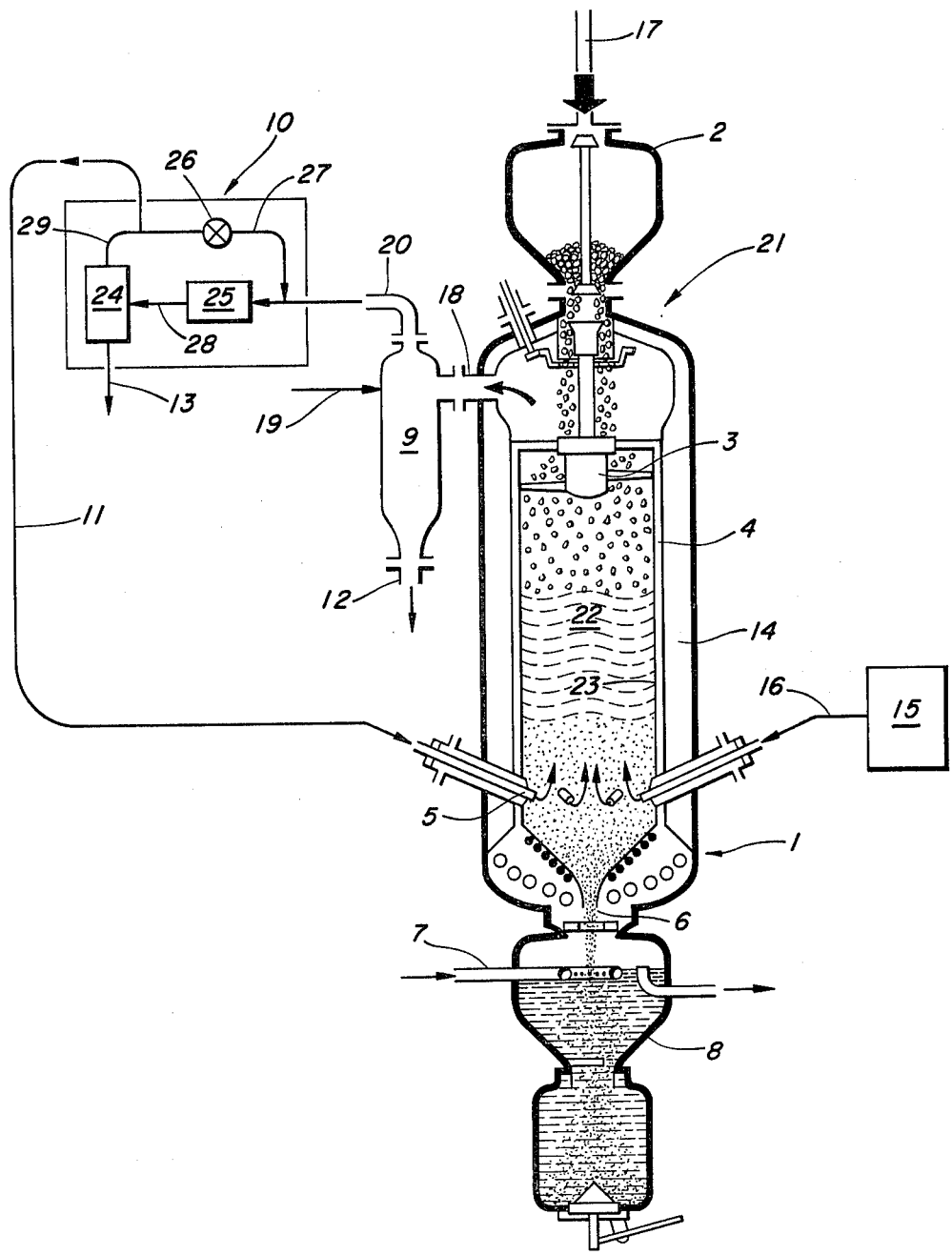

METHOD OF MAKING METHANOL USING A SLAGGING GASIFIER

BACKGROUND OF THE INVENTION

Anderson U.S. Pat. No. 4,195,978 discloses a coal slagging gasifier and method of operating improved by providing a slag removable orifice.

Bowden et al, Synthetic Fuels from Coal, Alternative Energy Sources Symposium, Feb. 9–13, 1980, discusses a Lurgi dry-bottom gasifier which in FIG. 1 is shown to produce crude synthesis gas. This gas enters a quench vessel in which the tars are condensed and particulate matter occludes to the tar. The water dissolves some of the phenols and ammonia, while gas exits the quenched scrubber at about 475° K. or less and passes through a waste heat boiler. At page 160 second paragraph from the bottom at item 5 under other disadvantages of the Lurgi gasifier. Bowden states that the synthesis gas from the Lurgi gasifier contains 8 to 15 percent by volume methane which must be removed or reformed before the gas can be used for chemicals manufacture. Also on page 160 Bowden et al mention that synthesis gas from Lurgi gasifiers can also be used to manufacture such chemicals as methanol.

Hempill et al U.S. Pat. No. 4,199,327 discloses coal gasification in a slagging gasifier with $CO_2$ and $H_2S$ removal wherein the final gas product is used for methanol production, power plant, methanation plant or chemical feedstock preparation purposes.

SUMMARY OF THE INVENTION

A process for producing methanol from solid carbonaceous material comprising providing a gasifier means and a methanol formation means connected to said gasifier means, said gasifier means comprising a gasification chamber defined by a gasification chamber wall having an upper and a lower portion, an upper chamber wall inlet means for feeding said solid carbonaceous material into said gasification chamber, a lower chamber wall gas injection means for introducing gas into said gasification chamber, and an upper chamber wall gas outlet means, said gas outlet being connected to a gas product conduit, said methanol formation means comprising a methanol formation reactor means, reactor output conduit means, condensor means, and condensor output conduit means, said reactor conduit means being connected to said lower chamber wall gas injection means, said condenser output conduit means being connected to said condenser means and to said methanol formation reactor means, said gas product conduit being connected to said condenser means.

The invention provides the benefit of converting coal almost exclusively to methanol.

A GENERAL DESCRIPTION OF THE FIGURE

The FIGURE shows a slagging gasifier in accordance with the present invention in schematic cross section.

DETAILED DESCRIPTION OF THE INVENTION

The FIGURE shows a slagging gasifier 1 in accordance with the present invention. Coal is fed into the coal hopper 2 and distributed by the coal distributor stirrer 3 within the refactory lining 4. The coal is gasified by the introduction through the tuyeres 5 of steam and/or oxygen. A slagging tap 6 is provided above circulating quench water inlet conduit 7 which provides water to the slag quench chamber 8. Synthesis gas is formed in the slagging gasifier and leaves the upper portion of the gasifier to enter gas quencher 9. In the gas quencher 9 tars are condensed and particulate matter occludes to the tar. The liquid and condensed solids and occluded solids leave the gas quencher through conduit 12. The remaining gas enters the methanol formation system 10. In the methanol formation system 10 methane is separated from the synthesis gas for example by forming methanol from the synthesis gas. The separated methane is recycled to the tuyeres 5 through the methane feed conduit 11.

Solid carbonaceous material is fed to the gasifier 1 through the solid carbonaceous material feed line 17. Such carbonaceous material for feeding through the solid carbonaceous material feed line 17 include coal. Oxidizing gas from oxidizing gas source 15 passes through oxidizing gas line 16 through tuyeres 5 and into the gasification chamber 22. The gasification chamber 22 is defined by gasification chamber walls 23. Steam and oxygen either alone or together as a gaseous mixture may be used as the oxidizing gas in oxidizing gas source 15. The gasifier 1 has a water jacket 14 for controlling the temperature in the gasification chamber 22.

The methanol producing system 21 includes in addition to the gasifier 1 the methanol formation system 10. Gasifier output gas leaves the gasification chamber 22 through the gasifier output gas line 18 which is connected to the scrubber 9. The scrubber 9 is provided with a scrubbing fluid line 19 through which scrubbing fluid passes into the scrubber and is used to scrub the gasifier output gas. The scrubbing fluid passes from the scrubber 9 into the scrubbing fluid outlet 12. Suitable scrubbing fluids include water and other scrubbing fluids known to be useful for diminishing the amount of hydrogen sulfide in gasifier output gas. The scrubbed gas leaves the scrubber 9 through the scrubber output gas line 20 which is connected to the methanol formation system 10. The methanol formation reactor 25 preferably contains catalytic material suitable for formation of methanol from hydrogen and carbon monoxide while unreacted methane accumulates in the residual gas. Methanol formed in the methanol formation system 10 passes through methanol product line 13. Residual methane feed line 11 is connected to methanol formation system 10 and conducts residual methane from the methanol formation system to at least one of the tuyeres 5. The methane returning to the gasification chamber 22 through the methane feed conduit 11 is reformed in the gasification chamber 22 into hydrogen and carbon monoxide.

The methanol formation system 10 comprises a methanol formation reactor bed 25 which preferably is provided with catalytic material. The methanol synthesis catalyst contained in the catalytic bed 25 can be any of those known in the art which are operable under specific converter pressure and reaction conditions typically methanol synthesis catalysts are copper containing. Examples of useful catalyst compositions and their temperatures and pressures of operation are listed by Bowman U.S. Pat. No. 4,226,795 at column 5 lines 25 through 33. The catalytic bed 25 is provided with the necessary means for obtaining the preferred reaction pressure and temperature for the catalysts chosen. For example, if a copper/zinc oxide/alumina catalyst is chosen a pressure of 51 atmospheres and a temperature of 250° C. would be appropriate. For further detail Bowman makes reference to U.S. Pat. Nos. 3,923,694 and 3,850,850. The methanol formed in the catalytic bed 25 passes through line 28 and is condensed in the condenser 24 to form liquid methanol which is removed from the condenser 24 through methanol product line 13. A portion of the uncondensed gas from the condenser may be passed through line 29 to valve 26 and then through line 27 to be recycled through methanol formation reactor bed 25. At least a portion of the gas in line 29 passes into and through line 11 which is connected to at least one of the tuyeres 5 for passing this portion into the gasification chamber 22.

A major portion of the uncondensed gas passing through line 29 and line 11 is methane. When this methane is returned to the gasification chamber 22 it is mixed with steam and/or oxygen in the presence of heat and thereby reformed into carbon monoxide and hydrogen. This methane contribution to the concentrations of hydrogen and carbon monoxide leaving the gasification chamber 22 through the gasifier output line 18 beneficially provides improvement in the efficiency of gasifier syn gas production which in turn beneficially provides improvement in the methanol yield from the methanol formation system 10 per unit of solid carbonaceous material feed to the gasifier 1 through feed line 17.

Having thus described the invention by reference to certain of its preferred embodiments it is respectfully pointed out that embodiments described are illustrative rather than limiting in nature and that many variations and modifications are possible within the scope of the present invention. Such variations and modifications may appear obvious and desirable to those skilled in the art upon a review of the foregoing description of preferred embodiments.

Having thus described the invention, I claim:

1. A process for producing methanol from solid coal consisting essentially of the steps as follows:
   (a) providing
      (i) a slagging gasifier (1),
      said slagging gasifier comprising a coal hopper (2), a coal distributor stirrer (3), tuyeres (5), a slag quench chamber wall enclosing a slag quench chamber (8), a circulating quench water inlet conduit (7) and a slagging tap (6),
      (ii) a gas quencher (9)
      (iii) methanol formation reactor (25)
      (iv) a condenser (24) and
      (v) valve (26)
   said coal hopper being disposed above said coal distributor strirrer,
   said coal distributor stirrer being disposed above said tuyeres,
   said slagging gasifier being connected to said gas quencher by gasifier output conduit (18),
   said gas quencher being connected to said methanol formation reactor by scrubber outlet gas conduit (20), said methanol formation reactor being connected by conduit (28) to said condenser, said condenser being connected by conduit (29) to said valve, said conduit (29) being connected to conduit (11),
   said conduit (11) being connected to said tuyeres and said valve being connected by conduit (27) to said scrubber output gas conduit,
   said methanol formation reactor containing catalyst suitable for formation of methanol from hydrogen and carbon monoxide,
   (b) gasifying said coal in said slagging gasifier by heating coal in said gasifier to form ash and gaseous gasifier output mixture comprising tar, solids, hydrogen sulfide, hydrogen, carbon monoxide and methane, said gasifying consisting of:
      (i) feeding said coal through said hopper and over said distributor stirrer,
      (ii) feeding steam, oxygen and an uncondensed gaseous mixture through said tuyeres,
      (iii) feeding water through said circulating quench water inlet conduit into said slag quench chamber to cool ash passing to said quench chamber,
   (c) contacting said gaseous gasifier output mixture with liquid water in said gas quencher to form a gaseous quencher output mixture comprising hydrogen, carbon monoxide and methane,
   (d) adding a recycle portion of gaseous condenser output mixture comprising hydrogen, carbon monoxide and methane to said gaseous methanol formation reactor feed mixture,
   (e) contacting said methanol formation catalyst with said gaseous methanol formation reactor feed mixture in said methanol formation reactor to form a condenser feed mixture comprising methanol vapor, methane, hydrogen and carbon monoxide,
   (f) condensing said methanol from said condenser feed mixture in said condenser to form liquid methanol product and a gaseous condenser output mixture comprising methane, hydrogen and carbon monoxide,
   (g) feeding a gasifier portion of said gaseous condenser output mixture into said slagging gasifier through said tuyeres,
   whereby liquid methanol is produced and substantially all of the methane formed is ultimately returned to said slagging gasifier.

2. A process for producing methanol from solid coal consisting of the steps as follows:
   (a) providing
      (i) slagging gasifier means
      (ii) gas quencher means
      (iii) methanol formation reactor means
      (iv) condenser means and
      (v) valve means
   said slagging gasifier means comprising
      a coal hopper means,
      coal distributor stirrer means,
      a plurality of tuyere means,
      slag quench chamber means,
      quench water inlet conduit means and
      slagging tap means,
   said coal hopper means being disposed above said coal distributor stirrer means, said coal distributor stirrer means being disposed above said tuyere means,
   said methanol formation reactor means containing catalyst suitable for formation of methanol from hydrogen and carbon monoxide,
   (b) gasifying said coal in said slagging gasifier by heating coal in said gasifier to form ash and gaseous gasifier output mixture comprising tar, solids, hydrogen sulfide, hydrogen, carbon monoxide and methane, said gasifying consisting of,
      (i) feeding said coal through said hopper and over said distributor stirrer, (ii) feeding steam, oxygen and an uncondensed gaseous mixture through said tuyeres, (iii) feeding water through said circulating quench water inlet conduit into said slag quench chamber to cool ash passing to said quench chamber, (c) contacting said gaseous gasifier output mixture with liquid water in said gas quencher to form a gaseous quencher output mixture comprising hydrogen, carbon monoxide and methane, (d) adding a recycle portion of gaseous condenser output mixture comprising hydrogen, carbon monoxide and methane to said gaseous methanol formation reactor feed mixture, (e) contacting said methanol formation catalyst with said gaseous methanol formation reactor feed mixture in said methanol formation reactor to form a condenser feed mixture comprising methanol vapor, methane, hydrogen, and carbon monoxide, (f) condensing said methanol from said condenser feed mixture in said condenser to form liquid methanol product and a gaseous condenser output mixture comprising methane, hydrogen and carbon monoxide, (g) feeding the balance of said gaseous condenser output mixture into said gasifier through said tuyeres, (h) conveying liquid methanol from said condenser means in a second condenser conduit means connected to said condenser, whereby liquid methanol is produced and substantially all of the methane formed is ultimately returned to said slagging gasifier.

* * * * *